United States Patent
Huang et al.

(10) Patent No.: US 10,544,452 B2
(45) Date of Patent: Jan. 28, 2020

(54) METHOD AND USE OF NUCLEIC ACID ISOTHERMAL AMPLIFICATION VIA A POLYMERASE SPIRAL REACTION

(71) Applicants: INSTITUTE OF PLA FOR DISEASE CONTROL AND PREVENTION, Beijing (CN); BEIJING ANZONE TECHNOLOGY CO., LTD., Beijing (CN)

(72) Inventors: Liuyu Huang, Beijing (CN); Wei Liu, Beijing (CN); Derong Dong, Beijing (CN); Zeliang Chen, Beijing (CN); Dayang Zou, Beijing (CN); Zhan Yang, Beijing (CN); Simo Huang, Beijing (CN); Ningwei Liu, Beijing (CN); Yaqing Xu, Beijing (CN); Yue Tang, Beijing (CN); Wen Ma, Beijing (CN)

(73) Assignees: INSTITUTE OF PLA FOR DISEASE CONTROL AND PREVENTION, Beijing (CN); BEIJING ANZONE TECHNOLOGY CO., LTD., Beijing (CN)

(*) Notice: Subject to any disclaimer, the term of this patent is extended or adjusted under 35 U.S.C. 154(b) by 234 days.

(21) Appl. No.: 15/518,480

(22) PCT Filed: Jul. 7, 2015

(86) PCT No.: PCT/CN2015/000493
§ 371 (c)(1),
(2) Date: Apr. 11, 2017

(87) PCT Pub. No.: WO2016/054870
PCT Pub. Date: Apr. 14, 2016

(65) Prior Publication Data
US 2017/0226574 A1 Aug. 10, 2017

(30) Foreign Application Priority Data

Oct. 11, 2014 (CN) .......................... 2014 1 0535579

(51) Int. Cl.
  C12Q 1/68 (2018.01)
  C12Q 1/6853 (2018.01)
  C12Q 1/6844 (2018.01)
  C12Q 1/686 (2018.01)

(52) U.S. Cl.
  CPC .......... C12Q 1/6853 (2013.01); C12Q 1/686 (2013.01); C12Q 1/6844 (2013.01)

(58) Field of Classification Search
  CPC ............ C12Q 1/6853; C12Q 2527/101; C12Q 2565/60
  See application file for complete search history.

(56) References Cited

U.S. PATENT DOCUMENTS 6,221,635 B1 * 4/2001 Rovera ................ C12Q 1/6837
                                                   435/5

FOREIGN PATENT DOCUMENTS

| CN | 102242197 A | 11/2011 |
| CN | 102260733 A | 11/2011 |
| CN | 104232622 A | 12/2014 |
| WO | WO 2005/118853 A2 | 12/2005 |
| WO | WO 2012/174192 A2 | 12/2012 |
| WO | WO 2016/054870 A1 | 4/2016 |

OTHER PUBLICATIONS

International Search Report, dated Oct. 8, 2015, in International Application No. PCT/CN2015/000493.
Written Opinion, dated Oct. 8, 2015, in International Application No. PCT/CN2015/000493.

* cited by examiner

*Primary Examiner* — David C Thomas
(74) *Attorney, Agent, or Firm* — Knobbe, Martens, Olson & Bear, LLP

(57) ABSTRACT

A nucleic acid isothermal amplification method is based on a polymerase spiral reaction using only one pair of primers. The method employs a self-spiraling amplification method, and has a high amplification efficiency.

23 Claims, 6 Drawing Sheets

Specification includes a Sequence Listing.

METHOD AND USE OF NUCLEIC ACID ISOTHERMAL AMPLIFICATION VIA A POLYMERASE SPIRAL REACTION

PRIORITY AND CROSS-REFERENCE TO RELATED APPLICATIONS

This application is the U.S. National Phase Application under 35 U.S.C. § 371 of International Application No. PCT/CN2015/000493, filed Jul. 7, 2015, designating the U.S. and published as WO 2016/054870 A1 on Apr. 14, 2016, which claims the benefit of Chinese Patent Application No. CN 201410535579.1, filed Oct. 11, 2014. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with a Sequence Listing as an ASCII text file via EFS-Web. The Sequence Listing is provided as a file entitled JEEK033001APCSEQLIST.txt, created and last saved on Apr. 11, 2017, which is 3,044 bytes in size. The information in the electronic format of the Sequence Listing is incorporated herein by reference in its entirety in accordance with 35 U.S.C. § 1.52(e).

TECHNICAL FIELD

The present invention belongs to a method of nucleic acid isothermal amplification in the technical field of molecular biology, and particularly relates to a method of nucleic acid isothermal amplification via a polymerase spiral reaction and the use thereof in nucleic acid (DNA or RNA) detection.

BACKGROUND

Polymerase chain reaction, i.e. PCR technique, is a method for rapidly amplifying a specific gene or DNA sequence in vitro, which was invented by the scientist K. B. Mullis from Department of Human Genetics at Cetus Corporation on 1983. PCR utilizes a thermotolerant DNA polymerase, mixes primers and a target DNA to massively amplify the target DNA in short time through cycles consisting of high temperature denaturation, low temperature annealing and appropriate temperature extension. PCR technique has advantages such as high specificity, sensitivity and yield, rapidity, simplicity, good repeatability, facilitation in automation. PCR technique can amplify a target gene or certain DNA fragment to be studied ten thousands and even million times in a tube in several hours, enabling direct observation and determination of the result with the naked eye. PCR technique can amplify sufficient amount of DNA from a hair, a drop of blood, even a cell for analysis, research, detection and identification. PCR technique is a revolutionary innovation and a landmark in the field of biological medicine, but it has no way to get rid of the restriction of thermal cycling. After a few decades of development, some isothermal nucleic acid amplification techniques are gradually invented.

The nucleic acid isothermal amplification technique is a technique that a target gene is massively replicated at constant temperature. At present, the methods for nucleic acid isothermal amplification mainly comprise the following methods. TAS, i.e. Transcript-based Amplification System, was developed in 1989 by SISKA Diagnostic Institute and Salk Institute from the United States; it is mainly applied for RNA amplification with a reaction principle that a target RNA is massively amplified under an action of reverse transcriptase and T7 RNA polymerase through multistep temperature change. During the amplification process, it mainly depends on the polymerase activity of the reverse transcriptase and the activity of RNase H, such amplification manner gets rid of the limitation of high temperature cycling, and only needs to set multistep temperature. The method is of greatly progressive significance, has high specificity and sensitivity. However, the reverse transcriptase and T7 RNA polymerase are required to be added continually during the reaction, which brings a great deal of inconvenience to use. Moreover, it can only be used for RNA amplification currently.

NASBA, i.e. Nucleic Acid Sequence-Based Amplification, was first introduced by Canadian Can-gene Corporation in 1991 in an article. NASBA is an isothermal amplification technique which can massively replicate nucleic acid sequence in vitro. NASBA is a stable and sustained enzymatic reaction medicated by two primers. NASBA reaction relies on AMV reverse transcriptase, RNase H, T7 RNA polymerase, the complete reaction is performed at the constant temperature (41° C.), and a desirable result may be obtained in 1.5-2 h. The drawbacks of NASBA are that there still requires a complex sequential procedure for products detection; the enzymes are not thermotolerant, and can be added only after the RNA chain is melted; nonspecific interaction of the primers due to low temperature causes nonspecific amplification; three enzymes are required to be added into the reaction and to be activated in the same reaction system at the same temperature.

3SR, i.e. Self-Sustained Sequence Replication, is also developed by SISKA Diagnostic Institute and Salk Institute of the United States based on TAS. It has a principle substantially similar to that of TAS, except that RNase H is needed, and, the reaction also requires AMV reverse transcriptase and T7 RNA polymerase. Compared to NASBA, 3SR is more complex, and its sensitivity is not high. NASBA is gradually replacing 3SR.

SDA, i.e. Strand Displacement Amplification, was established by American scholar Wallker, et al in 1992. It utilizes the capability of restriction enzyme of shearing DNA recognition site and that of DNA polymerase of extending from the nick to 3' end and substituting the downstream sequence to massively amplify a target sequence under isothermal condition. The drawbacks of SDA are that there still a need for denaturation process, the target sequence to be amplified cannot exceed 200 bp, and the follow-on detection is complex.

RCA, i.e. Rolling Circle Amplification, was invented in 1998. The inspiration of this method mainly derives from the replication process of a circular DNA of a microorganism in the nature, which is invented by simulating amplification of such circular DNA in vitro. The method can massively amplify a target sequence mainly with DNA polymerase by ingenious primer design. However, its amplification products are very complicated, and have various sizes of the fragments. Since RCA can only amplify a circular DNA template, its application range is greatly restricted.

HDA, i.e. Helicase-Dependent Amplification, is an in vitro isothermal nucleic acid amplification technique, first introduced by researchers Vincent, et al. from New England Biolabs Incorporation of the United States in 2004. Its reaction principle lies in that the double stranded DNA was opened under the action of a helicase, and a single strand DNA binding protein binds the template single strand, which makes the DNA keep a single strand state, then primers bind to the single strand for extending forward under the action of DNA polymerase. However, HAD amplification also requires three enzymes, which greatly limits its application scope.

SPIA, i.e. Single Primer Isothermal Amplification, was invented in 2005. With the technique, a single stranded cDNA is massively amplified by a hybrid with a DNA fragment at 3' end and a RNA fragment at a 5' end under actions of RNase H and DNA polymerase having strong strand displacement activity. SPIA amplification is performed at a temperature of about 60° C., and completed in half of an hour. SPIA amplification technique has the advantages of high amplification efficiency, strong conservation, simple principle, etc, and is adapted for nucleic acid detection, nucleic acid sequencing, SNP detection, single stranded template preparation and gene chip probe preparation, etc.

A novel in vitro nucleic acid amplification technique, i.e. Loop-mediated Isothermal Amplification (LAMP), was established by Notomi, et al. in 2000. Such novel amplification method requires at least 4 primers, at most 6 primers to specificity identify 6, 7 or 8 regions of a target fragment, and amplifies the target sequence under the action of chain displacement of a DNA polymerase in short time. Such technique has properties of simplicity, specificity, efficiency and rapidity. When the target DNA is massively synthesized, byproduct, i.e. white magnesium pyrophosphate precipitate, is produced, which makes LAMP reaction be directly judged as a negative or positive result by a change of turbidity. PCR requires two primers to specifically bind two sections of a target sequence, while LAMP specifically binds 6 to 8 sections, having stronger specificity than PCR. LAMP is 10-100 fold more sensitive than common PCR, which is comparable to fluorescent quantitative PCR. Moreover, LAMP amplification is performed in isothermal condition, a thermostable device (such as an isothermal water bath kettle, an isothermal metal bath, etc) can meet the reaction requirement, thereby greatly reducing detection cost. Since LAMP technique was reported, it has been widely applied to detection of microorganisms such as bacterium, fungus, virus, etc, diagnosis of genetic disease, and early determination of gender in a short period of more than ten years.

The results of comparison of various isothermal amplification techniques are shown in Table 1 for detail.

TABLE 1

The results of comparison of various isothermal amplification techniques

| Name | Invention time | Number of enzymes required | Application range | PubMed[x] |
|---|---|---|---|---|
| Transcript-based Amplification System (TAS) | 1989 | 2 | RNA | 44 |
| Self-Sustained Sequence Replication (3SR) | 1990 | 3 | DNA and RNA | 245 |
| Nucleic Acid Sequence-Based Amplification (NASBA) | 1991 | 3 | DNA and RNA | 2782 |
| Strand Displacement Amplification (SDA) | 1992 | 3 | DNA and RNA | 267 |
| Rolling Circle Amplification (RCA) | 1998 | 1 | circular DNA and RNA | 541 |
| Loop-mediated Isothermal Amplification (LAMP) | 2000 | 1 | DNA and RNA | 934 |
| Helicase-Dependent Amplification (HDA) | 2004 | 3 | DNA | 99 |
| Single Primer Isothermal Amplification (SPIA) | 2005 | 3 | DNA and RNA | 137 |

[x]Note:
PubMed represents the number of articles searched on PubMed in term of English full name of various isothermal amplificationtechniques, by the end of Mar. 25, 2014.
LAMP is predominant in these isothermal nucleic acid amplification methods, but the LAMP products are too complex, and recovery and sequencing of the LAMP products are very difficult, they cannot be directly sequenced like common PCR products. Since LAMP products are the amplification mixture that is extremely complex and irregular, LAMP products cannot be used for cloning. These defects make LAMP be limited in gene rapid detection.

SUMMARY

An object of the present invention is to provide primers of nucleic acid isothermal amplification via polymerase spiral reaction for target sequence amplification.

The primers of nucleic acid isothermal amplification via polymerase spiral reaction for target sequence amplification provided by the present invention comprise a specific primer pair.

The specific primer pair consists of a primer FP and a primer BP, the target sequence of the specific primer is named as target sequence A.

The primer FP sequentially consists of an N region and an F region from a 5' end to a 3' end, the F region is identical or complementary to 15-30 bp nucleotides of the target sequence A from a 3' terminal.

The primer BP sequentially consists of an N' region and a B region from a 5' end to a 3' end, the B region is complementary or identical to 15-30 bp nucleotides of the target sequence A from a 5' terminal.

The N' region is a reverse non-complementary sequence of the N region. The N region is not identical or complementary to the F region; the N' region is not identical or complementary to the B region.

The above primers also comprise p pair(s) of accelerating primer pair A, the target sequence of each the accelerating primer pair A is a certain segment in the target sequence A, which is named as a target segment B, upstream primer and downstream primer of each accelerating primer pair A are not overlapped with the F region or the B region, p is an integer that is greater than or equal to 1.

An upstream primer in the above accelerating primer pair A is identical or complementary to 15-30 bp nucleotides of the target segment B from the 3' terminal, the downstream primer in the accelerating primer pair A is identical or complementary to 15-30 bp nucleotides of the target segment B from the 5' terminal. The above primer also comprises m accelerating primer pairs B; the target sequence of each the accelerating primer pair B is named as targent fragment C, which is a certain segment in the target sequence A.

An upstream primer of the accelerating primer pair B sequentially consists of an N1 region and a B-1 region from a 5' end to a 3' end, the B-1 region is identical or complementary to 15-30 bp nucleotides of the targent fragment C from the 3' terminal; the B-1 region is not overlapped with the F region or the B region.

A downstream primer of the accelerating primer pair B sequentially consists of an N1' region and a B-2 region from a 5' end to a 3' end, the B-2 region is complementary or identical to 15-30 bp nucleotides of the targent fragment C from a 5' terminal; the B-2 region is not overlapped with the F region or the B region.

The N1 region is not identical or complementary to B-1 region; the N1' region is not identical or complementary to the B-2 region.

The N1' region is a reverse non-complementary sequence of the N1 region.

The targent fragment C and the targent fragment B are same or different;

m is an integer that is greater than or equal to 1.

The above primers are as follows:
1) specific primer
2) specific primer and p accelerating primer(s) A;
3) specific primer and m accelerating primers B;
4) specific primer, p accelerating primer(s) A and m accelerating primer(s) B; and the targent fragment B of the accelerating primer A and the targent fragment C of the accelerating primer B are different.

The target sequence A comprises a Bc region, a Bc1 region, . . . , a Bcn-1 region, a Bcn region, a Fcn region, a Fcn-1 region, . . . , a Fc1 region, a Fc region from 5' end to 3' end;

n is greater than or equal to 2.

The primer FP sequentially consists of a N region and a F region from a 5' end to a 3' end, the F region is identical or complementary to a Fc region the in a target sequence from a 3' terminal (15-30 bp nucleotides of the target sequence A from a 3' terminal).

The primer BP sequentially consists of an N' region and a B region from a 5' end to a 3' end, the B region is complementary or identical to a Bc region in a target sequence from a 5' terminal (15-30 bp nucleotides of the target sequence A from a 5' terminal); the N' region is a reverse non-complementary sequence of the N region.

The primer $A_{up}$ is identical or complementary to any region adjacent to FC region between the BC region and the FC region of the target sequence.

The primer $A_{down}$ is complementary or identical to any region adjacent to the BC region between the BC region and the FC region of the target sequence.

Any region adjacent to FC region between the BC region and the FC region of the target sequence (a portion adjacent to 3' end of the target segment B) is an Fcn region, an Fcn-1 region, . . . , an Fc1 region.

Any region adjacent to BC region between the BC region and the FC region of the target sequence (a portion adjacent to 5' end of the target segment B) is a Bc1 region, . . . , a Bcn-1 region, a Bcn region;

p is an integer that is greater than or equal to 1.

The primer $B_{up}$ sequentially consists of an N1 region and a B-1 region from 5' end to 3' end.

The B-1 region is identical or complementary to any region adjacent to the FC region between the BC region and the FC region of the target sequence (a portion adjacent to 3' end of the target segment C).

The primer $B_{down}$ sequentially consists of an N1' region and a B-2 region from the 5' end to 3' end.

The B-2 region is complementary or identical to any region adjacent to the BC region between the BC region and the FC region of the target sequence (a portion adjacent to the 5' end of the target segment C);

m is an integer that is greater than or equal to 1.

Among the above primers, the target sequence is Sequence 1 (SEQ ID NO.1) in the Sequence listings.

The primers consist of specific primer pair and an accelerating primer A pair.

The nucleotide sequence of the primer FP in the specific primer pair is Sequence 2 (SEQ ID NO.2).

The nucleotide sequence of the primer BP in the specific primer pair is Sequence 3 (SEQ ID NO.3).

The nucleotide sequence of the primer $A_{up}$ in the accelerating primer A is Sequence 7 (SEQ ID NO.7).

The nucleotide sequence of the primer $A_{down}$ in the accelerating primer A is Sequence 8 (SEQ ID NO.8).

Another object of the present invention is to provide a reagent of nucleic acid isothermal amplification via polymerase spiral reaction for target sequence amplification.

The reagent provided by the present invention, comprises the above primers, Tris.HCl, KCl, $(NH_4)_2SO_4$, Tween 20, betaine, $MgSO_4$, dNTPs and DNA polymerase.

The molar ratio of each primer in the primers is in equal proportion in the above reagent.

The above reagent also comprises a reverse transcriptase.

The third object of the present invention is to provide a kit of nucleic acid isothermal amplification via polymerase spiral reaction for target sequence amplification.

The kit provided by the present invention, comprises the above primers or the above reagent.

A use of the above primers or the above reagent or the above kit for detecting whether a sample to be detected contains a target nucleic acid molecules is also within the protection scope of the present invention.

A use of the above primers or the above reagent or the above kit for preparing a product that detects whether a sample to be detected contains a target nucleic acid molecules is also within the protection scope of the present invention.

The fourth object of the present invention is to provide a method for detecting whether a sample to be detected contains a target nucleic acid molecule.

The method provided by the present invention is A or B:

A comprises the following steps:
1) extracting nucleic acids in a sample to be detected;
2) performing an amplification using the above reagent with the nucleic acids as a template, to obtain amplification reaction products;
3) detecting the amplification reaction products using a real time turbidimeter, if the real time turbidity detection curve of the amplification reaction products rises, the sample to be detected contains or candidately contains a target nucleic acid molecule;

If the real time turbidity detection curve of the amplification reaction products does not rise, the sample to be detected does not contain or not candidately contain a target nucleic acid molecule.

B comprises the following steps:
1) extracting nucleic acids in a sample to be detected;
2) performing an amplification using the above reagent, and the nucleic acids as a template, and adding a chromogenic agent when the amplification is performed, to obtain amplification reaction products;
3) observing the amplification reaction products with the naked eye, if the amplification reaction products develop a color, the sample to be detected contains or candidately contain a target nucleic acid molecule.

If the amplification reaction products do not develop a color, the sample to be detected does not contain or not candidately contain a target nucleic acid molecule. In the above method, a condition for the amplification is an isothermal reaction at 60-65° C. for 120-150 mins.

In the above method, the nucleic acid is DNA or RNA.

The fifth object of the present invention is to provide a method for nucleic acid isothermal amplification via polymerase spiral reaction.

In the method provided by the present invention, a pair of oligonucleotide primers are used, in which nucleotide fragments that are reversed to each other are added to a 5' end of the primers. Nucleic acid isothermal amplification via polymerase spiral reaction is performed for a target gene in the presence of primers and a DNA polymerase under isothermal condition to self-spirally extend the target gene, so as to complete nucleic acid amplification.

In the above method, the primers of the polymerase spiral reaction comprise a pair of primers that consist of a forward primer FP and a backward primer BP.

The primer FP consists of a F region and a N region, the F region is complementary to a Fc region of a target sequence, the N region is a special sequence that may derive from the target sequence itself, and may also derive from an exogenous sequence, but it must be same as the N region sequence of 5' end of the BP primer.

The primer BP consists of a B region and a N region, the B region is complementary to a Bc region of a target sequence, the N region is a special sequence that may derive from the target sequence itself, and may also derive from an exogenous sequence, but it must be same as the N region sequence of 5' end of the FP primer. In the above method, the reaction process of the method for nucleic acid isothermal amplification via polymerase spiral reaction and the special primer thereof is as follows:

1) A self spiral ring structure is formed sequentially using the primers FP and BP:

(1) The reaction is carried out in an isothermal environment of 60° C.-65° C., double strands of a target sequence are unlocked into two single strands, the F region of the primer FP binds to a Fc portion of a single strand from 3' end to 5' end, and extends toward the 3' end to form a sequence Bc complementary to the B region of the single strand from 3' end to 5' end, and a successive sequence, that is, gradually forming a double stranded structure, then the double stranded structure is unlocked to form two single strands, i.e. an intermediate single strand that comprises the N region, the F region and the Bc region from 5' end to 3' end, and a single strand of the target sequence from 3' end to 5' end;

(2) The primer BP binds to the intermediate single strand that comprises the N region, the F region and the Bc region from 5' end to 3' end, B portion in BP complementarily binds to the Bc region of the intermediate single strand, and extends toward 3' end to form a Fc region complementary to the F region and a Nc region complementary to the N region, forming a double stranded structure. When the double stranded structure is unlocked to form single strands, two single strands are formed, thus a key target single strand is formed in nucleic acid isothermal amplification via polymerase spiral reaction, i.e. a single strand that comprises the Nc region, the Fc region, the B region and the N region from 3' end to 5' end.

(3) The Nc region and N region at two ends of the target single strand are complementary, and a self spiral ring structure is formed after the Nc region binds the N region, since Nc terminal is at the 3' end, a self spiral extension can be performed using the Nc terminal itself as a template. Once a self spiral ring structure is formed, an aggressive nucleic acid isothermal amplification via polymerase spiral reaction begins. The amplification may be completed in about 5 mins, and spiral amplification products with different sizes are formed, thereby the nucleic acid amplification is completed finally.

2) At the same time, a self spiral ring structure may also be formed sequentially using primers BP and FP:

(1) The reaction is carried out in an isothermal environment of 60° C.-65° C., double strands of the target sequence are unlocked into two single strands, the B portion of the primer BP binds to a Bc portion of a single strand end from 3' to 5' end, and extends toward the 3' end to form a sequence Fc complementary to the F region of the single strand from 3' end to 5' end, and a successive sequence, that is, gradually forming a double stranded structure, then the double stranded structure is unlocked to form two single strands, i.e. a intermediate single strand that comprises the N region, the B region and the Fc region from 5' end to 3' end, and a single strand of the target sequence from 3' end to 5' end.

(2) The primer FP binds to the intermediate single strand that comprises the N region, the B region and the Fc region from 5' end to 3' end, F portion in FP complementarily binds to the Fc region of the intermediate single strand, and extends toward 3' end to form a Bc region complementary to the B region and a Nc region complementary to the N region, forming a double stranded structure. When the double stranded structure is unlocked to form single strands, two single strands are formed, thus a key target single strand is formed in nucleic acid isothermal amplification via polymerase spiral reaction, i.e. a single strand that comprises the N region, the F region, the Bc region and the Nc region from 5' end to 3' end.

(3) The Nc region and the N region at two ends of the target single strand are complementary, and a self spiral ring structure is formed after the Nc region binds the N region, since Nc terminal is at the 3' end, a self spiral extension using the Nc terminal itself as a template. Once a self spiral ring structure is formed, an aggressive nucleic acid isothermal amplification via polymerase spiral reaction begins. The amplification may be completed in about 5 mins, and spiral amplification products with different sizes are formed, thereby the nucleic acid amplification is completed finally.

In the above method, the target gene is NDM-1 gene or H1N1 gene; The FP primer for detecting NDM-1 gene is shown as sequence 2 (SEQ ID NO:2) in Sequence listings, the BP primer is shown as sequence 3 (SEQ ID NO:3) in Sequence listings;

The FP primer for detecting H1N1 gene is shown as sequence 5 (SEQ ID NO:5) in Sequence listings, the BP primer is shown as sequence 6 (SEQ ID NO:6) in Sequence listings.

The sixth object of the present invention is to provide a method for detecting whether a sample to be detected contains a target genome DNA by nucleic acid isothermal amplification via polymerase spiral reaction and a turbidimetry.

The method provided by the present invention comprises the following steps:

1) preparing 23 μL PSR reaction solution comprising the components as follows: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amount of the added PSR primers is 40 pM for FP and BP respectively;

2) extracting the nucleic acids from a sample to be detected to obtain a nucleic acid extraction solution whose concentration is greater than or equal to 20 ng/μL)

adding 2 μL of the nucleic acid extraction solution to the PSR reaction solution prepared in step 1) to make the final reaction volume be 25 μL, mixing the reaction solution, adding a sealant to prevent contamination;

4) performing the isothermal amplification reaction in an environment of 60-65° C., with a reaction time being 120-150 mins;

5) recording the change in turbidity in the reaction tube using a real time turbidimeter, judging the sample whose curve rises as a positive result, and the sample whose curve does not rise as a negative result.

The seventh object of the present invention is to provide a method for detecting whether a sample to be detected contains a target genome DNA using a method for nucleic acid isothermal amplification via polymerase spiral reaction and a color development method.

The method provided by the present invention comprises the following steps:

1) preparing 23 μL PSR reaction solution comprising the components as follows: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amount of the PSR primers added is 40 pM for FP and BP respectively;

2) extracting the nucleic acids from a sample to be detected to obtain a nucleic acid extraction solution which has a concentration of greater than or equal to 20 ng/μL)

3) adding 2 μL of the nucleic acid extraction solution and 1 μL color development solution to the PSR reaction solution prepared in step 1) to make the final reaction volume be 26 μL, mixing the reaction solution, adding a sealant to prevent contamination;

4) performing the isothermal amplification reaction in an environment of 60-65° C., with a reaction time being 120-150 mins;

5) taking out the reaction tube, observing it with the naked eye or with the help of ultraviolet light, the sample whose reaction solution has a color change is a positive result, the sample whose reaction solution has no color change is a negative result.

The eighth object of the present invention is to provide a method for detecting whether a sample to be detected contains RNA using a method for nucleic acid isothermal amplification via polymerase spiral reaction and a turbidimetry or a color development method.

The method the provided by the present invention comprises the following steps:

1) preparing 23 μL PSR reaction solution comprising components as follows: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase and reverse transcriptase, the amount of the PSR primers added is 40 pM for FP and BP respectively;

2) extracting the nucleic acids from a sample to be detected to obtain a nucleic acid extraction solution which has a concentration of greater than or equal to 20 ng/μL)

3) adding 2 μL of the nucleic acid extraction solution to the PSR reaction solution prepared in step 1), mixing the reaction solution, adding a sealant to prevent contamination;

4) performing the isothermal amplification reaction in an environment of 60-65° C., with a reaction time being 120-150 mins;

5) judging the reaction result using turbidimetry or color development method.

In the above method, the sealant is columnar fully-refined solid paraffin block or half-refined solid paraffin block which has a melting point lower than a temperature for nucleic acid isothermal amplification reaction by 0-25° C., and a diameter being same as the reaction tube caliber.

The method for using the sealant: the paraffin block is added above the reaction solution in the reaction tube, and the tube is capped to perform the reaction.

By studying intensively the above nucleic acid amplification method, and for the defects existing in the prior art, the present invention provides a new method for nucleic acid isothermal amplification via polymerase spiral reaction (PSR).

The above sealant (patent application number: 201210371448.5, publication number is CN102936623A) is a columnar fully-refined solid paraffin block or half-refined solid paraffin block which has a melting point lower than a temperature for nucleic acid isothermal amplification reaction by 0-25° C., and a diameter being same as reaction tube caliber. The method for using the sealant: the paraffin block is added above the reaction solution in the reaction tube, and the tube is capped to perform the reaction.

The present invention is further explained in combination with the specific examples.

DETAILED DESCRIPTION

The present invention provides a method for nucleic acid isothermal amplification via polymerase spiral reaction, wherein a pair of oligonucleotide primers are used, nucleotide fragments that are reversed to each other are added to the 5' end of two primers of the pair of primers, respectively, polymerase spiral reaction is performed for a target gene in the presence of primers and DNA polymerase under isothermal condition to self spirally extend the target gene, so as to complete the nucleic acid amplification.

Figure 1:
FIG. 1 is a schematic diagram of fundamental primers for polymerase spiral reaction.
Figure 2:
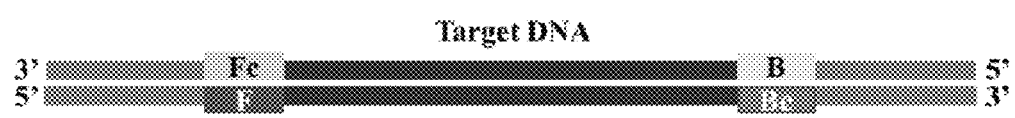
FIG. 2 is a region division of the PSR primer design.

As shown in FIG. 1 (N in BP in the figure should be changed to N'), the fundamental primers for polymerase spiral reaction only comprise a pair of primers, a forward primer FP and a backward primer BP. Primers design is very similar to that of common PCR. As shown in FIG. 2, F and B are primer design regions, between which is a extension region. Polymerase spiral reaction (self spiral chain reaction) can begin as long as it is in the direction of these two primers.

FP (Forward Primer): this primer consists of a F region and a N region, the F region is complementary to a Fc region of a target sequence, the N region is a special sequence that may derive from non-BC region or FC region in the target sequence, and may also derive from an exogenous sequence, but it must be reversed and not complementary to the N' region sequence of 5'end of the BP primer, which is the key in polymerase spiral reaction.

BP (Backward Primer): this primer consists of a B region and a N' region, the B region is complementary to a Bc region of a target sequence, the N' region is a fragment that is reversed and not complementary to the N region.

Specific design principles of primers required in nucleic acid isothermal amplification via polymerase spiral reaction are as follows.

The following specific primer pairs are designed according to a target sequence. The target sequence comprises a Bc region, a Bc1 region, . . . , a Bcn-1 region, a Bcn region, an Fcn region, an Fcn-1 region, . . . , a Fc1 region, a Fc region from a 5' end to a 3' end; n is greater than or equal to 2.

The above specific primer pair consists of a primer FP and a primer BP, the target sequence of the specific primers is designated as target sequence A.

The above primer FP sequentially consists of a N region and a F region from a 5' end to a 3' end, the F region is identical or complementary to 15-30 bp nucleotides (FC) of the target sequence A from a 3' terminal.

The above primer BP sequentially consists of an N' region and a B region from a 5' end to a 3' end, B region is complementary or identical to 15-30 bp nucleotides (BC) of the target sequence A from a 5' terminal.

Figure 3:
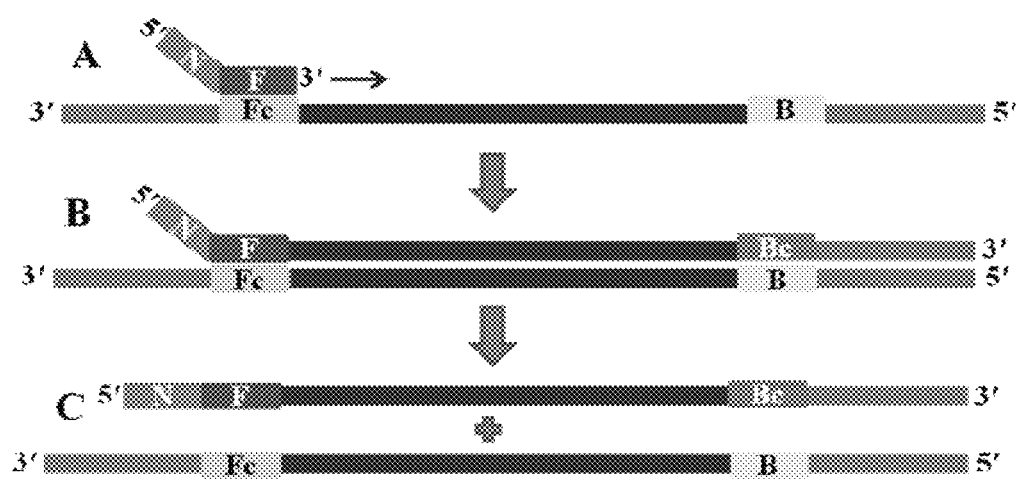
FIG. 3 is a principle schematic diagram (1) of PSR amplification using FP primers.
Figure 7:
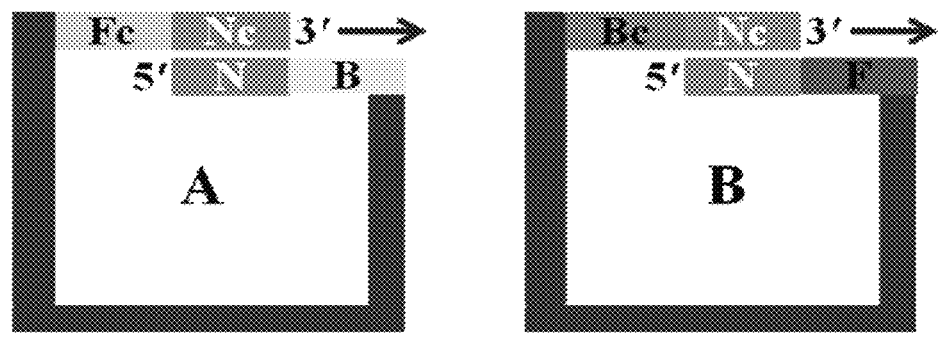
FIG. 7 is a structure schematic diagram of PSR self spiral ring.

The above N' region is a reverse non-complementary sequence of the N region. The reaction process and principle of the method for nucleic acid isothermal amplification via polymerase spiral reaction (PSR) and the special primers thereof are as follows:

1) A self spiral ring structure in FIG. 7A is formed sequentially by primers FP and BP:

1.1) As shown in FIG. 3A, the reaction is carried our in an isothermal environment (60° C.-65° C.), double strands of a target sequence are unlocked into two single strands, the F region in a primer FP binds to the Fc portion of a single strand from 3' to 5' end, and extends toward the 3' end to form a sequence Bc complementary to the B region of the single strand from 3' end to 5' end, and a successive sequence, that is, gradually forming a double stranded structure in FIG. 3B, then the double stranded structure in FIG. 3B is unlocked to form two single strands in FIG. 3C, i.e. a intermediate single strand that comprises the N region, the F region and the Bc region from 5' end to 3' end, and a single strand of the target sequence from 3' end to 5' end.

Figure 4:
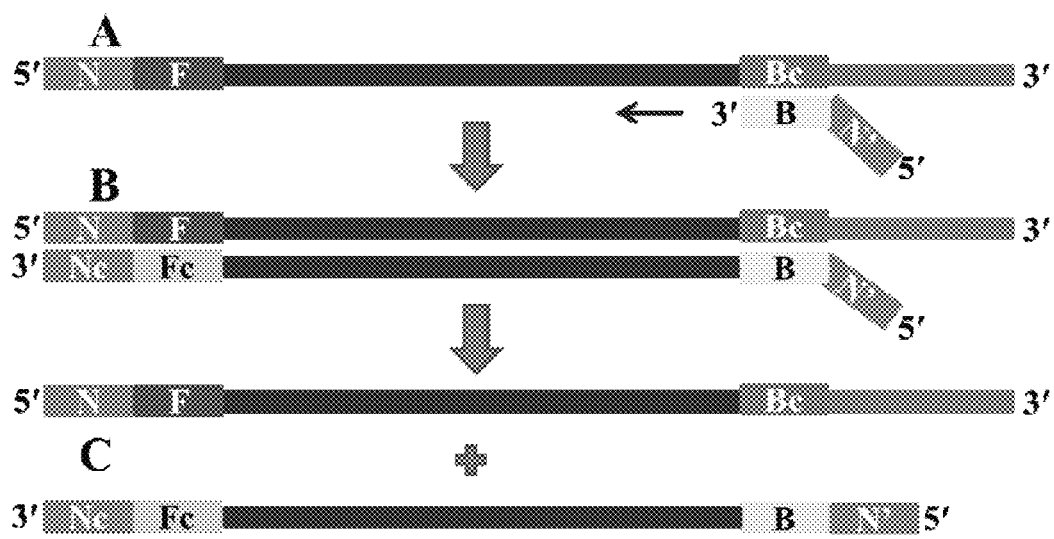
FIG. 4 is a principle schematic diagram (2) of PSR amplification using FP primers.

1.2) As illustrated in FIG. 4A, the primer BP binds to the intermediate single strand that comprises the N' region, F region and the Bc region from 5' end to 3' end in FIG. 3C, B portion in BP complementarily binds to the Bc region of the intermediate single strand, and extends toward 3' end to form a Fc region complementary to the F region and a Nc region complementary to the N region, forming a double stranded structure in FIG. 4B. When the double stranded structure in FIG. 4B is unlocked to form single strands, two single strands in FIG. 4C are formed, thus a key target single strand is formed in a polymerase spiral reaction, i.e. a single strand that comprises the Nc region, the Fc region, the B region and the N region from 3' end to 5' end in the bottom of FIG. 4C.

Figure 8:
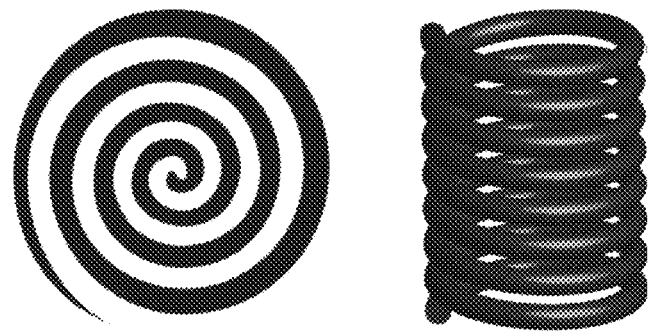
FIG. 8 is a schematic diagram of PSR reaction products.

1.3) As can be seen from FIG. 4C, the Nc region and N region at two ends of the target single strand are complementary, so they (the Nc region and the N region) bind to each other to form a self spiral ring structure in FIG. 7A. Since Nc terminal is at the 3' end, a self spiral extension may be performed using the Nc terminal itself as a template. Once a self spiral ring structure is formed, an aggressive polymerase spiral reaction begins. The amplification may be completed in about 5 mins, and spiral amplification products with different sizes as shown in FIG. 8 are formed, thereby the nucleic acid amplification is completed finally.

Figure 5:
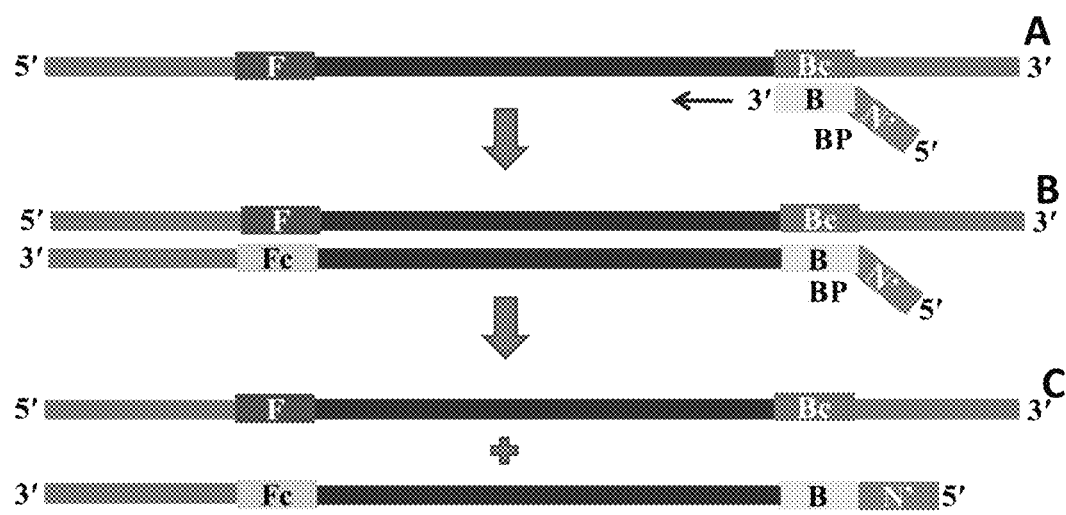
FIG. 5 is a principle schematic diagram (1) of PSR amplification using BP primers.

2) At the same time, a self spiral ring structure in FIG. 7B may also be formed sequentially using primers BP and FP:

2.1) As shown in FIG. 5A, the reaction is carried out in an isothermal environment (60° C.-65° C.), double strands of the target sequence are unlocked into two single strands, the B portion of the primer BP binds to the Bc portion of a single strand from 3' end to 5' end, and extends toward the 3' end to form a sequence Fc complementary to the F region of the single strand from 3' end to 5' end, and a successive sequence, that is, gradually forming a double stranded structure in FIG. 5B, then the double stranded structure in FIG. 5B is unlocked to form two single strands in FIG. 5C, i.e. a intermediate single strand that comprises the N region, the B region and the Fc region from 5' end to 3' end, and a single strand of the target sequence from 3' end to 5' end.

Figure 6:
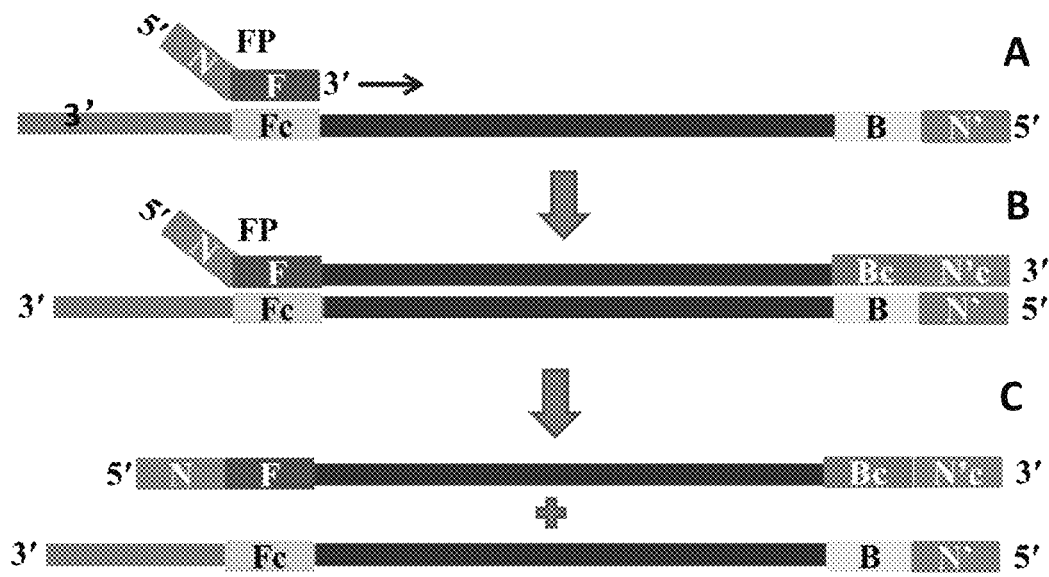
FIG. 6 is a principle schematic diagram (2) of PSR amplification using BP primers.

2.2) As shown in FIG. 6A, the primer FP binds to the intermediate single strand that comprises the N region, the B region and the Fc region from 5' end to 3' end in FIG. 3C, F portion in FP complementarily binds to the Fc region of the intermediate single strand, and extends toward 3' end to form a Bc region complementary to the B region and a Nc region complementary to the N region, forming a double stranded structure in FIG. 6B. When the double stranded structure in FIG. 6B is unlocked to form single strands, two single strands in FIG. 6C are formed, thus a key target single strand is formed in the polymerase spiral reaction, i.e. a single strand that comprises the N region, the F region, the Bc region and the Nc region from 5' end to 3' end in the top of FIG. 6C.

2.3) As shown in FIG. 6C, the Nc region and N region at two ends of the target single strand are complementary, so they (the Nc region and the N region) bind to each other to form a self spiral ring structure in FIG. 7B. Since Nc terminal is at the 3' end, a self spiral extension can be carried out using the Nc terminal itself as a template. Once a self spiral ring structure is formed, an aggressive polymerase spiral reaction begins. The amplification may be completed in about 5 mins, and spiral amplification products with different sizes as shown in FIG. 8 are formed, thereby the nucleic acid amplification is completed finally.

All the methods used in the following examples are the conventional methods, unless particularly explained otherwise. The particular steps may be seen in: 《Molecular Cloning: A Laboratory Manual》 (Sambrook, J., Russell, David W., Molecular Cloning: A Laboratory Manual, 3rd edition, 2001, NY, Cold Spring Harbor) for reference.

The primers used are synthesized by Takara Bio.

Examples are carried out on the premise of the technical solution of the present invention, and detailed embodiments and specific operation process are provided. Examples will be helpful to understand the present invention, but the protection scope of the present invention is not limited to the following examples.

Example 1. Polymerase Spiral Reaction (PSR) was Used to Detect Whether a Sample to be Detected Contains a NDM-1 Gene NDM-1 gene was taked as an example, polymerase spiral reaction (PSR) was used to detect whether a sample to be detected contained a target gene (DNA). The samples to be detected were 4 positive samples and 4 negative samples. The positive samples were 4 repetitions of aqueous solution that contained NDM-1 gene (concentration: 56 ng/μL); 4 negative samples were 4 repetitions of ultrapure water. Specific method comprised the following steps:

I. PSR Primer Design

The nucleotide sequence (GenBank number: FN396876) of NDM-1 gene was obtained by searching American gene database, GenBank, homology analysis was carried out by BLAST software, a conserved target sequence (Sequence 1 (SEQ ID NO:1) in the Sequence listings) was found, and PSR primers were designed based on the conserved target sequence.

Like the common PCR, a pair of primers F and B were first designed, the F primer: 5'-GGTCGATACCGCCTG-GAC-3', the B primer: 5'-GCATGCAGCGCGTCCA-3'. Then a universal exogenous sequence N was added to the 5' ends of both primers, in which a sequence N (5'-3': ACGAT-TCGTACATAGAAGTATAG) was added to the F primer to form a primer FP, and a sequence N (5'-3': GATATGAAGA-TACATGCTTAGCA) was added to the B primer to form a primer BP. The primer sequences are shown in Table 2.

TABLE 2

| PSR primer sequences for NDM-1 gene amplification | |
|---|---|
| Primer name | Sequence (5'-3') |
| FP | ACGATTCGTACATAGAAGTATAG(N region)-GGTCGATACCGCCTGGAC (F region) (Sequence 2 (SEQ ID NO: 2) in the Sequence listings) |
| BP | GATATGAAGATACATGCTTAGCA(N' region)-GCATGCAGCGCGTCCA (B region) (Sequence 3 (SEQ ID NO: 3) in the Sequence listings) |

II. Polymerase Spiral Reaction (PSR) and Turbidimetry Were Used to Detect Whether a Sample to be Detected Contained a NDM-1 Gene.

1. Preparing 23 μL PSR reaction solution comprising the components as follows: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amount of the PSR primers added is 40 pM for FP and BP each, respectively.

2. Extracting the nucleic acids in the sample to be detected according to the conventional method which has a concentration of greater than 20 ng/μL.

3. Adding 2 μL of the nucleic acid extraction solution into the PSR reaction solution prepared in step 1 to make the final reaction volume be 25 μL, mixing the reaction solution, adding a sealant (the sealant is a columnar fully-refined solid paraffin block or half-refined solid paraffin block which has a melting point lower than a temperature for nucleic acid isothermal amplification reaction by 0-25° C., and a diameter being same as reaction tube caliber, and the method for using the sealant: the paraffin block is added above the reaction solution in the reaction tube, and the tube is capped to perform the reaction) to prevent aerosol contamination.

4. Performing a isothermal amplification reaction in an environment of 63° C. (60-65° C. may be OK) (such as a water bath kettle, metal bath, etc), with a reaction time being 120 min (120-150 mins may be OK).

5. Recoding a change in turbidity in the reaction tube by a real time turbidimeter, judging a sample whose curve rises as a positive result, and a sample whose curve does not rise as a negative result.

Figure 9:
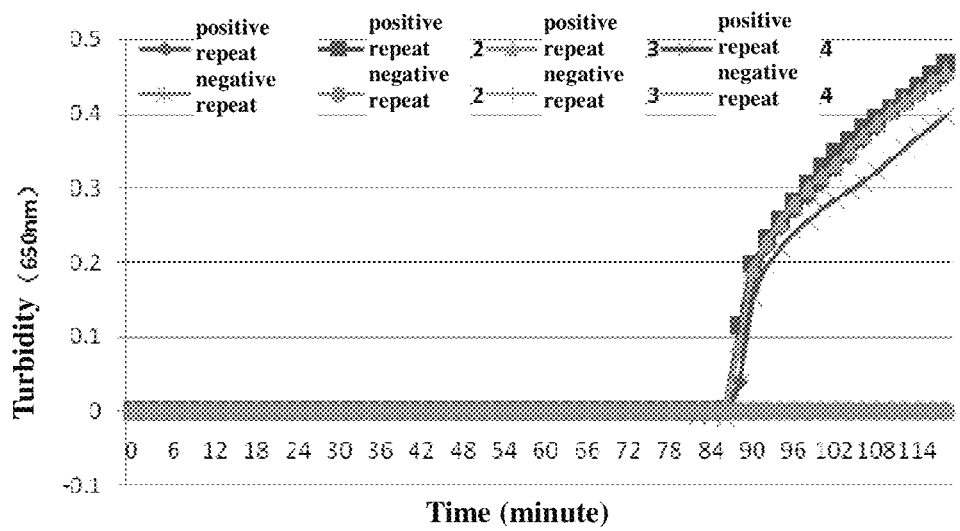
FIG. 9 is a PSR reaction result of DNA amplification using two primers.
Figure 10:
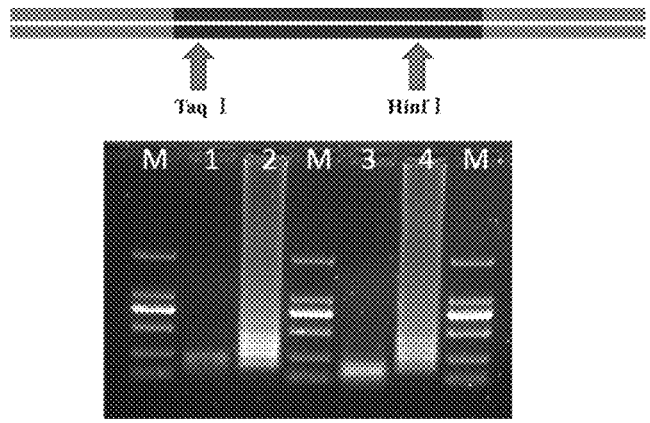
FIG. 10 is an enzymatic cleavage verification result of PSR amplification products.

The results were shown in FIG. 9, the four positive samples all showed rised turbidity curve, while the four negative samples maintained zero turbidity unchanged, which was consistent with the expection.

III. Polymerase Spiral Reaction (PSR) and Color Development Method Were Used to Detect Whether a Sample to be Detected Contained a NDM-1 Gene.

1. Preparing a 23 μL PSR reaction solution comprising the components at the following concentrations: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amount of the PSR primers added is 40 pM for FP and BP each, respectively.

2. Extracting the nucleic acids from a sample to be detected according to the conventional method, and the concentration of the nucleic acid is greater than 20 ng/μL.

3. Adding 2 μL of the nucleic acid extraction solution (the concentration is greater than 20 ng/μL) and 1 μL color development solution (mainly some metal ion indicators that may produce a change in color depending on a change in $Mg^{2+}$ concentration in the reaction solution, such as calcein/$Mn^{2+}$ mixed liquor, hydroxynaphthol blue, etc; also comprising some nucleic acid dyes, such as SYBR Green I, etc) to the PSR reaction solution prepared in step 1 to make the final reaction volume be 26 μL, mixing the reaction solution, adding a sealant (the sealant is a columnar fully-refined solid paraffin block or half-refined solid paraffin block which has a melting point lower than nucleic acid isothermal amplification reaction temperature by 0-25° C., an a diameter being same as reaction tube caliber, and the method of using the sealant: the paraffin block is added above the reaction solution in the reaction tube, and the tube is capped to perform the reaction) to prevent aerosol contamination.

4. Performing an isothermal amplification reaction in an environment of 63° C. (60-65° C. may be OK) (such as a water bath kettle, metal bath, etc), with a reaction time being 120 min (120-150 mins may be OK).

5. Taking out the tube, observing it with the naked eye or with the help of ultraviolet light, and a sample whose reaction solution has a color change is a positive result, a sample whose reaction solution has no color change is a negative result.

The results: the color of reaction solutions of the four positive samples had changed, and the color of reaction solutions of the four negative samples was unchanged, which was consistent with the expection.

IV. Enzymatic Cleavage Verification of the Amplification Products of Polymerase Spiral Reaction (PSR)

Two enzyme cutting sites were found in NDM-1 target sequence, enzyme cutting sites Taq I and Hinf I. After the PSR amplification products obtained in step II or step III were cleaved by these two enzymes respectively, the products from cleavage by the enzymes were subjected to 1% agarose gel electrophoresis. The results were shown in FIG.

10 (Lane 1 was a product digested by Taq I, Lane 3 was a product digested by Hinf I, Lane 2 and Lane 4 were PSR amplification products). As can be seen, the PSR amplification products that were not digested by the enzymes presented a diffuse arrangement in the lanes (self spiral reaction would produce numerous circular amplification products with various lengths, the size of the fragments was 150 bp to ten thousands bp, thus presenting a diffuse arrangement in the lane), while single band was obtained after enzyme digestion (the circular amplification products with various length were incessant repetitions of the same target sequence, and the target sequence contained enzyme cutting site, so a product of only one size of fragment remained after enzyme digestion, presenting a single band in the electrophoresis), which showed that the above PSR amplification principle was correct, and PSR was practicable.

Example 2. Polymerase Spiral Reaction (PSR) was Used to Detect Whether a Sample to be Detected Contained RNA Detecting H1N1 virus was taked as an example, polymerase spiral reaction (PSR) was used to detect whether a sample to be detected contained RNA. The samples to be detected were 2 positive samples and 2 negative samples. 2 positive samples were sample 1 that was infected with H1N1 and sample 2 that was infected with H1N1; 2 negative samples were throat swabs 1 and 2 from healthy humans, respectively.

Specific method comprised the following steps:

I. PSR Primer Design

The nucleotide sequence (GenBank number: KM361419.1) of H1N1 gene was obtained by searching American gene database, GenBank, homology analysis was carried out by BLAST software, a conserved target sequence (Sequence 4 (SEQ ID NO:4) in the Sequence listings) was found, and PSR primers were designed based on the conserved target sequence.

Like the common PCR, a pair of primers F and B were first designed, the F primer: 5'-GCAATGAGAACTAT-TGGGACTC-3', the B primer: 5'-ATTTGCTGCAATGAC-GAGAG-3'. Then a universal exogenous sequence N was added to 5' end of the both primers, a sequence N (5'-3': ACGATTCGTACATAGAAGTATAG) was added to the F primer to form a primer FP, and a sequence N'(5'-3': GATAT-GAAGATACATGCTTAGCA) was added to the B primer to form a primer BP. The primer sequences are shown in Table 3.

TABLE 3

PSR primer sequences for H1N1 gene amplification

| Primer name | Sequence (5'-3') |
|---|---|
| FP | ACGATTCGTACATAGAAGTATAG(N region)-GCAATGAGAACTATTGGGACTC (Sequence 5 (SEQ ID NO: 5) in the Sequence listings) |
| BP | GATATGAAGATACATGCTTAGCA(N' region)-ATTTGCTGCAATGACGAGAG (Sequence 6 (SEQ ID NO: 6) in the Sequence listings) |

II. Polymerase Spiral Reaction (PSR) and Turbidimetry Were Used to Detect Whether a Sample to be Detected Contained a H1N1 Target Gene.

1. Preparing a 23 µL PSR reaction solution comprising the components at the following concentrations: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase and a reverse transcriptase, the amount of the PSR primers added is 40 pM for FP and BP each, respectively.

2. Extracting the nucleic acids from a sample to be detected according to the conventional method, and the concentration of the nucleic acid is greater than 20 ng/µL.

3. Adding 2 µL of the nucleic acid extraction solution to the PSR reaction solution prepared in step 1 to make the final reaction volume be 25 µL, mixing the reaction solution, adding a sealant (the sealant is a columnar fully-refined solid paraffin block or half-refined solid paraffin block which has a melting point lower than a temperature for nucleic acid isothermal amplification reaction by 0-25° C., and a diameter being same as reaction tube caliber, and the method of using the sealant: the paraffin block is added above the reaction solution in the reaction tube, and the tube is capped to perform the reaction) to prevent aerosol contamination.

4. Performing a isothermal amplification reaction in an environment of 63° C. (60-65° C. may be OK) (such as a water bath kettle, metal bath, etc), with reaction time being 120 min (120-150 mins may be OK).

5. Recroding a change in turbidity in the reaction tube with a real time turbidimeter, judging a sample whose curve rised as a positive result, and a sample whose curve did not rise as a negative result.

Figure 11:
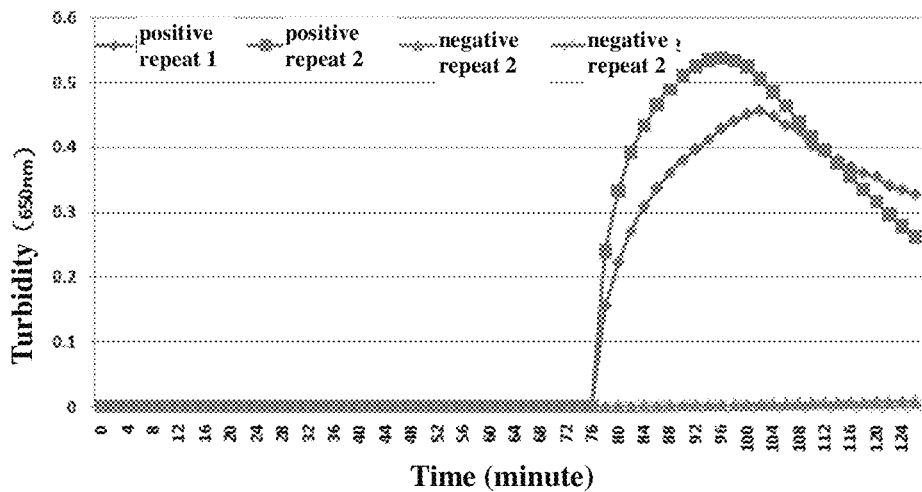
FIG. 11 is a PSR reaction result of RNA amplification using two primers.

The results were shown in FIG. 11, two positive samples all showed rised turbidity curve, and two negative samples maintained zero turbidity unchanged, which was consistent with the expection.

III. Polymerase spiral reaction (PSR) and color development method were used to detect whether a sample to be detected contained a H1N1 target gene.

1. Preparing a 23 µL PSR reaction solution comprising the components as follows: 20 mM Tris.HCl (pH 8.8), 10 mM KCl10 mM $(NH_4)_2SO_4$, 0.1% Tween 20, 0.8 M betaine, 8 mM $MgSO_4$, 1.4 mM dNTP each, 8 U Bst DNA polymerase and a reverse transcriptase, the amount of the PSR primers added is 40 pM for FP and BP each, respectively.

2. Extracting the nucleic acids from a sample to be detected according to the conventional method, in which the concentration of the nucleic acid is greater than 20 ng/µL.

3. Adding 2 µL of the nucleic acid extraction solution (the concentration is greater than 20 ng/µL) and 1 µL color development solution (mainly some metal ion indicators that may produce a change in color depending on a change in $Mg^{2+}$ concentration in the reaction solution, such as calcein/ $Mn^{2+}$ mixed liquor, hydroxynaphthol blue, etc; also comprising some nucleic acid dyes, such as SYBR Green I, etc) to the PSR reaction solution prepared in step 1 to make the final reaction volume be 26 µL, mixing the reaction solution, adding a sealant (the sealant is a columnar fully-refined solid paraffin block or half-refined solid paraffin block which has a melting point lower than nucleic acid isothermal amplification reaction temperature by 0-25° C., and a diameter being same as reaction tube caliber, and the method for using the sealant: the paraffin block is added above the reaction solution in the reaction tube, and the tube is capped to perform the reaction) to prevent aerosol contamination.

4. Performing a isothermal amplification reaction in an environment of 63° C. (60-65° C. may be OK) (such as a water bath kettle, metal bath, etc), with a reaction time being 120 min (120-150 mins may be OK).

5. Taking out the reaction tube, observing it with the naked eye or with the help of ultraviolet light, and a sample whose reaction solution has a color change is a positive result, the sample whose reaction solution has unchanged color is a negative result.

The results: the color of the reaction solution of two positive samples was changed, and the color of the reaction solution of two negative samples was unchanged, which was consistent with the expection.

Example 3. Primer Design for the Accelerating Polymerase Spiral Reaction

Figure 12:
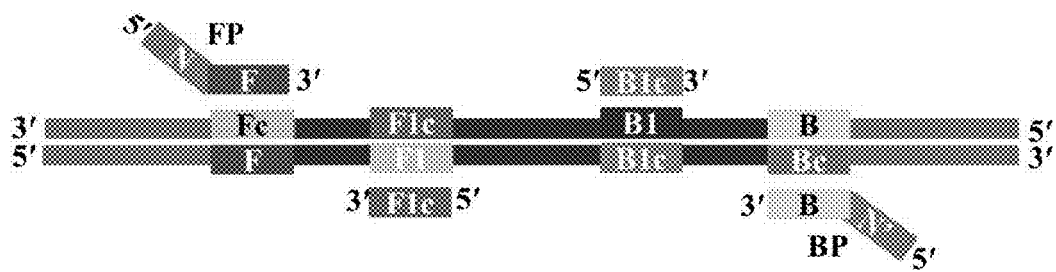
FIG. 12 is a schematic diagram of accelerating primers for self spiral isothermal chain reaction.

FIG. 12 is a schematic diagram of accelerating primers for self spiral isothermal chain reaction.

Figure 13:
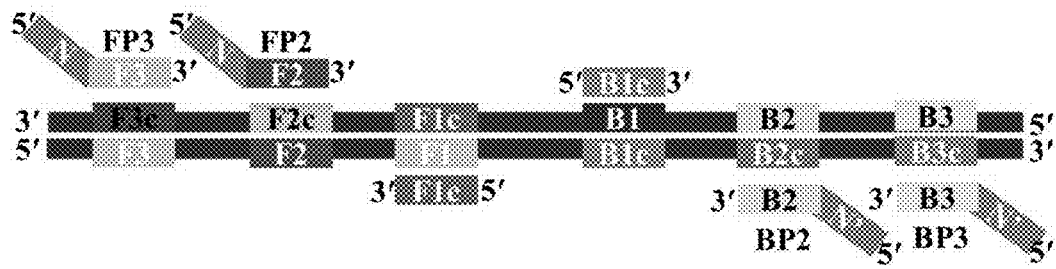
FIG. 13 is a schematic diagram of several primer combinations for self spiral isothermal chain reaction.
Figure 13:
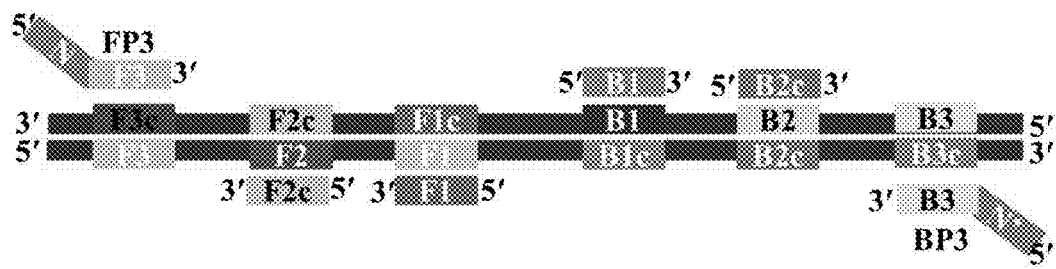

FIG. 13 is a schematic diagram of several primer combinations for self spiral isothermal chain reaction.

Figure 14:
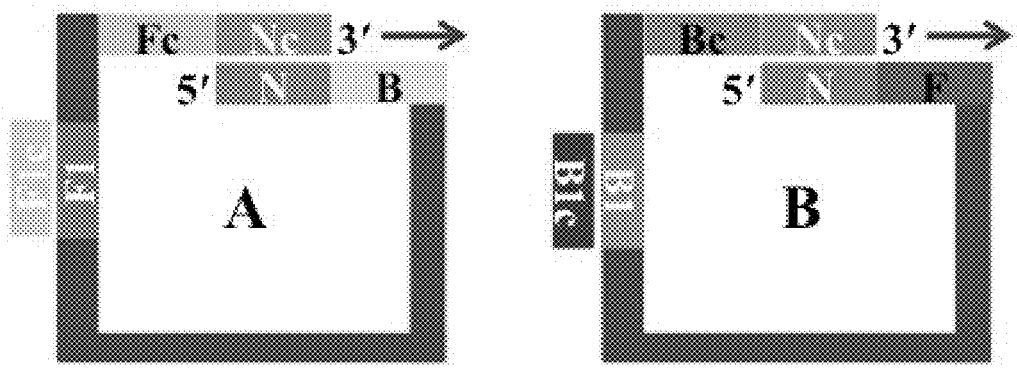
FIG. 14 is a principle diagram of PSR reaction accelerated by accelerating primers.

FIG. 14 is a principle diagram of PSR reaction accelerated by accelerating primers.

I. The Design Principle of Primers for Target Sequence Amplification in the Accelerating Polymerase Spiral Reaction The primers for the accelerating polymerase spiral reaction comprise specific primer pair and at least one of an accelerating primer group A and an accelerating primer group B.

The specific primer pair consists of a primer FP and a primer BP, the target sequence of the specific primer is designated as target sequence A.

The primer FP sequentially consists of a N region and a F region from a 5' end to a 3' end, the F region is identical or complementary to 15-30 bp nucleotides (FC region) from 3' end of the target sequence A.

The primer BP sequentially consists of a N' region and a B region from a 5' end to a 3' end, the B region is complementary or identical to 15-30 bp nucleotides (BC region) from 5' end of the target sequence A.

The N' region is a reverse non-complementary sequence of the N region.

The primers also comprise p pairs of accelerating primer pair A, the target sequence of each the accelerating primer pair A is certain segment in the target sequence A, which is designated as a target segment B, and upstream primer and downstream primer of each accelerating primer pair A are not overlapped with the F region or the B region, p is an integer that is greater than or equal to 1.

The upstream primer of the accelerating primer pair A is identical or complementary to 15-30 bp nucleotides of the target segment B from 3' terminal, the downstream primer of the accelerating primer pair A is complementary or identical to 15-30 bp nucleotides of the target segment B from 5' terminal.

The primers also comprise m accelerating primer pairs B; the target sequence of each of the accelerating primer pairs B is designated as targent fragment C, which is certain segment in the target sequence A.

The upstream primer of the accelerating primer pair B sequentially consists of a N1 region and a B-1 region from a 5' end to a 3' end, the B-1 region is identical or complementary to 15-30 bp nucleotides of the targent fragment C from 3' terminal; the B-1 region is not overlapped with the F region or the B region.

The downstream primer of the accelerating primer pair B sequentially consists of N1' region and B-2 region from a 5' end to a 3' end, the B-2 region is complementary or identical to 15-30 bp nucleotides of the targent fragment C from a 5' terminal; the B-2 region is not overlapped with the F region or the B region.

The N1' region is a reverse non-complementary sequence of the N1 region.

The targent fragment C and the targent fragment B are same or different;

m is an integer that is greater than or equal to 1.

Any region adjacent to FC region between the BC region and the FC region of the target sequence is a portion adjacent to 3' end of the target fragment B or the target fragment A.

Any region adjacent to BC region between the BC region and the FC region of the target sequence is a portion adjacent to 5' end of the target fragment B or the target fragment A.

The target sequence comprises a Bc region, a Bc1 region, ..., a Bcn-1 region, a Bcn region, a Fcn region, a Fcn-1 region, ..., a Fc1 region, a Fc region from a 5' end to a 3' end;

p and m are both greater than or equal to 1;

n is greater than or equal to 2.

II. System for Accelerating Polymerase Spiral Reaction and the Use Thereof

1. A System for Accelerating Polymerase Spiral Reaction Amplification and Reaction Condition A system for accelerating polymerase spiral reaction amplification was a 23 μL PSR reaction solution (the solvent was water) comprising the components at the following concentrations: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amounts of the FP primer, the BP primer, a primer $A_{up}$ and a primer $A_{down}$ was 40 pM, respectively.

When RNA was detected by the above accelerating polymerase spiral reaction amplification system, 8 U reverse transcriptase might be further added.

The reaction condition for the accelerating polymerase spiral reaction: isothermal amplification reaction was carried our in an environment 60-65° C. (such as a water bath kettle, metal bath, etc), and a reaction time was 120-150 mins.

2. Method for Nucleic Acid Isothermal Amplification Via Accelerating Polymerase Spiral Reaction (PSR)

1) The Method for Detecting Whether a Sample to be Detected Contained a Target Gene (DNA) Using Turbidimetry (1) Preparing 23 μL PSR reaction solution comprising the components at following concentrations: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amount of the PSR primers added is 40 pM for FP and BP, respectively.

(2) Extracting the nucleic acids from a sample to be detected according to the conventional method, and the concentration the nucleic acids is greater than 20 ng/μL.

(3) Adding 2 μL of the nucleic acid extraction solution to the PSR reaction solution prepared in step (1) to make the final reaction volume be 25 μL, mixing the reaction solution, adding a sealant to prevent aerosol contamination.

(4) Performing a isothermal amplification reaction in a 60-65° C. environment (such as a water bath kettle, metal bath, etc), with a reaction time being 120-150 mins.

(5) Recroding a change in turbidity in the reaction tube using a real time turbidimeter, judging a sample whose curve rised as a positive result, and a sample whose curve did not rise as a negative result.

2) The Method for Detecting Whether a Sample to be Detected Contained a Target Gene (DNA) Using Color Development Method (1) Preparing 23 µL PSR reaction solution comprising the components at the following concentrations: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amount of the PSR primers added is 40 pM for FP and BP, respectively.

(2) Extracting nucleic acids from a sample to be detected according to the conventional method, and the concentration of nucleic acids is greater than 20 ng/µL.

(3) Adding 2 µL of the nucleic acid extraction solution and 1 µL color development solution (mainly some metal ion indicators that may produce a change in color depending on a change in $Mg^{2+}$ concentration in the reaction solution, such as calcein/$Mn^{2+}$ mixed liquor, hydroxynaphthol blue, etc; also comprising some nucleic acid dyes, such as SYBR Green I, etc) to the PSR reaction solution prepared in step 1) to make the final reaction volume be 26 µL, mixing the reaction solution, adding a sealant to prevent contamination.

(4) Performing an isothermal amplification reaction in 60-65° C. environment (such as a water bath kettle, metal bath, etc), with a reaction time being 120-150 mins.

(5) Taking out the reaction tube, observing it with the naked eye or with the aid of ultraviolet light, a sample whose reaction solution has a color change is a positive result, and a sample whose reaction solution has no color change is a negative result.

3) The Method of Detecting Whether a Sample to be Detected Contained a Target RNA Using Turbidity The only difference compared to 1) was that 8 U reverse transcriptase was added to the PSR reaction solution.

4) The Method of Detecting Whether a Sample to be Detected Contained a Target RNA Using Color Development Method The only difference compared to 2) was that 8 U reverse transcriptase was added to the PSR reaction solution.

Example 4. Accelerating Polymerase Spiral Reaction (PSR) was Used to Detect Whether a Sample to be Detected Contained NDM-1 Gene NDM-1 gene was taken as an example, accelerating polymerase spiral reaction (PSR) was used to detect whether a sample to be detected contained a target gene (DNA), the specific method comprised the following steps:

I. The Primers of Accelerating Polymerase Spiral Reaction for NDM-1 Gene Amplification When NDM-1 gene was taken as an example, the method for detecting whether a sample to be detected contained NDM-1 gene via PSR reaction: firstly, the nucleotide sequence (GenBank number: FN396876) of NDM-1 gene was obtained by searching American gene database, GenBank, homology analysis was carried out by BLAST software, and a conserved target sequence (Sequence 1 (SEQ ID NO:1) in the Sequence listings) was found, secondly, primers for accelerating polymerase spiral reaction were designed according to the conserved target sequence and the design principle in the above I.

The primers for accelerating polymerase spiral reaction consisted of a specific primer pair and an accelerating primer pair A.

The specific primer pair consisted of a primer FP and a primer BP.

The primer FP: 5'-3' ACGATTCGTACATAGAAG-TATAG-GGTCGATACCGCCTGGAC (a N region was at positions 1-23; a F region was at positions 24-43, and the F region was identical to positions 531-548 of the target sequence) (Sequence 2 (SEQ ID NO:2))

The primer BP: 5'-3' GATATGAAGATACATGCT-TAGCA-GCATGCAGCGCGTCCA (a reverse non-complementary fragment of the N region was at positions 1-23, a B region was at positions 24-41, the B region was complementary to positions 451-469 of the target sequence Sequence 1 (SEQ ID NO:1)) (Sequence 3 (SEQ ID NO:3)).

The accelerating primer pair A consisted of a primer $A_{up}$ (Sequence 7 (SEQ ID NO: 7)) and a primer $A_{down}$ (Sequence 8 (SEQ ID NO: 8)).

The primer $A_{up}$ was identical to a Bc1 region (nucleotides at positions 531-548 of the target sequence Sequence 1 (SEQ ID NO: 1)) in the target sequence. See Table 4 for details.

The primer $A_{down}$ was complementary to an Fc1 region (nucleotides at positions 451-469 of the target sequence Sequence 1 (SEQ ID NO: 1)) in the target sequence. See Table 4 for details.

TABLE 4

The sequences of PSR primers for NDM-1 gene were as follows:

| Primer name | Sequence (5'-3') |
|---|---|
| FP | ACGATTCGTACATAGAAGTATAG-GGTCGATACCGCCTGGAC (Sequence 2 (SEQ ID NO: 2)) |
| BP | GATATGAAGATACATGCTTAGCA-GCATGCAGCGCGTCCA (Sequence 3 (SEQ ID NO: 3)) |
| primer $A_{up}$ | TCCAGTTGAGGATCTGGG (Sequence 7 (SEQ ID NO: 7)) |
| primer $A_{down}$ | GCATCAGGACAAGATGGGC (Sequence 8 (SEQ ID NO: 8)) |

II. Method of Detecting Whether a Sample to be Detected Contained NDM-1 Gene by Accelerating Polymerase Spiral Reaction and Turbidimeter An aqueous solution of NDM-1 gene at a concentration of 56 ng/µL was used as a sample to be detected.

Water was a negative control.

1. Preparing 23 µL PSR reaction solution comprising the components at the following concentrations: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8 U Bst DNA polymerase, the amount of the PSR primers added is 40 pM for FP and BP each, 20 pM for primer $A_{up}$ and primer $A_{down}$ each, respectively.

2. Extracting the nucleic acids from a sample to be detected according to the conventional method.

3. Adding 2 µL of the nucleic acid extraction solution to the PSR reaction solution prepared in step 1 to make the final reaction volume be 25 µL, mixing the reaction solution, adding a sealant specially made by the applicant (Patent No.: 201210371448.5) to prevent aerosol contamination.

4. Performing a PSR amplification in a real time turbidimeter instrument at 65° C. for 90 mins.

5. Reading and determining the result by the real time turbidimeter instrument.

Figure 15:
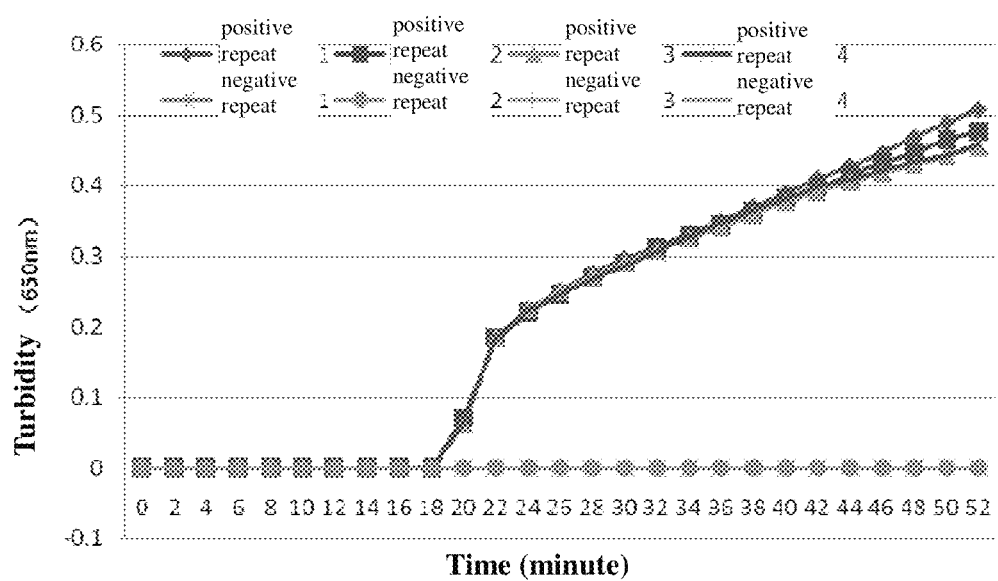
FIG. 15 is a PSR reaction containing two basic primers and two accelerating primers.

The amplification result was shown in FIG. 15, there was a rise of the turbidity curve for 4 positive repetitions (aqueous solution of NDM-1 gene), whereas the negative control remained zero turbidity unchanged, and the peak time was greatly advanced after addition of a pair of accelerating primers.

Compared to the result without the addition of the accelerating primers (FIG. 5), as could be seen, without addition of the accelerating primers (FIG. 9), the time when PSR took place was at 85$^{th}$ min, after the addition of a pair of accelerating primers (FIG. 15), the time when PSR took place was at 18$^{th}$ min, which was advanced by 67 mins, demonstrating that the accelerating primers might greatly accelerate the reaction of PSR.

The present invention provides a novel method for nucleic acid isothermal amplification, named as polymerase spiral reaction (Polymerase Spiral Reaction, PSR), the present invention has the following advantages:

1. The amplification reaction may be carried out in an isothermal environment, and a water bath kettle or an isothermal metal bath may meet the experiment requirement.

2. Simple primer design, only one pair of primers is needed to complete nucleic acid amplification. If one pair of accelerating primers is added, the reaction time will be greatly reduced. PSR user can complete primer design with common PCR primer design software (such as Primer5, DNAMAN, etc), and can complete amplification reaction only by adding one pair of universal exogenous genes (N) to the 5'end of PCR primers.

3. High sensitivity, the present invention is applicable to detection of a sample with low nucleic acid content such as virus.

4. High efficient amplification, the amount of DNA amplified can reach 0.6 μg/μL.

5. Simple operation, the experiment result may be observed by the naked eye by a real time turbidimeter instrument or calcein/$Mn^{2+}$ color development solution.

6. Broad variability of the size of the target fragment to be amplified, the amplification may be carried out for fragments of 100 bp to 200 bp.

7. The reaction time may be greatly reduced after addition of accelerating primers.

To sum up, the present invention provides a new technical platform for nucleic acid detection, and the amplification products are simple. The present invention not only is applied to the detection field, but also performs cloning recovery and sequencing for the amplification products after a little treatment. Thus method may be applied to all the fields which require nucleic acid amplification, and has a wide market prospect and great economic and social benefit, and is appropriate for widespread popularization and application.

What is claimed is:

1. A set of primers for a nucleic acid isothermal amplification via a polymerase spiral reaction for a target sequence amplification, comprising a specific primer pair;
the specific primer pair comprising a primer FP and a primer BP, wherein a target sequence of the specific primer pair is designated as a target sequence A;
the primer FP sequentially comprises an N region and an F region from a 5' end to a 3' end, wherein the F region is identical or complementary to 15-30 nucleotides of the target sequence A from a 3' terminal end;
the primer BP sequentially comprises an N' region and an B region from a 5' end to a 3' end, wherein the B region is complementary or identical to 15-30 nucleotides of the target sequence A from a 5' terminal end; and
the N' region is a reverse non-complementary sequence of the N region;
wherein the set of primers further comprises p pairs of accelerating primer pairs A, wherein a target sequence of each accelerating primer pair A is a certain segment in the target sequence A, which is designated as a target segment B, and an upstream primer and a downstream primer of each accelerating primer pair A do not overlap with the F region or the B region, wherein p is an integer that is greater than or equal to 1.

2. The set of primers according to claim 1, wherein an upstream primer of accelerating primer pair A is identical or complementary to 15-30 nucleotides of the target segment B from the 3' terminal end, and the downstream primer of the accelerating primer pair A is complementary or identical to 15-30 nucleotides of the target segment B from the 5' terminal end.

3. The set of primers according to claim 2, wherein the set of primers further comprises m accelerating primer pairs B, wherein a target sequence of each accelerating primer pair B is designated as a target segment C, which is a certain segment in the target sequence A; wherein:
an upstream primer of the accelerating primer pair B sequentially comprises an N1 region and a B-1 region from a 5' end to a 3' end, the B-1 region is identical or complementary to 15-30 nucleotides of the target segment C from the 3' terminal end; the B-1 region does not overlap with the F region or the B region;
a downstream primer of the accelerating primer pair B sequentially comprises a N1' region and a B-2 region from a 5' end to a 3' end, the B-2 region is complementary or identical to 15-30 nucleotides of the target segment C from a 5' terminal end; the B-2 region does not overlap with the F region or the B region;
the N1' region is a reverse non-complementary sequence of the N1 region;
the target segment C and the target segment B are either the same or different; and
m is an integer that is greater than or equal to 1.

4. The set of primers according to claim 3, wherein the target sequence is comprises SEQ ID NO: 1;
The set of primers comprises a specific primer pair and one accelerating primer pair A;
the nucleotide sequence of the primer FP in the specific primer pair is SEQ ID NO: 2;
the nucleotide sequence of the primer BP in the specific primer pair is SEQ ID NO: 3;
the nucleotide sequence of an upstream primer of the accelerating primer pair A is SEQ ID NO: 7;
the nucleotide sequence of a downstream primer of the accelerating primer pair A is SEQ ID NO: 8.

5. A reagent for a nucleic acid isothermal amplification via a polymerase spiral reaction for a target sequence amplification, comprising the set of primers of claim 4, Tris.HCl, KCl, $(NH_4)_2SO_4$, Tween 20, betaine, $MgSO_4$, dNTPs and DNA polymerase;
the molar ratio of each primer in the set of primers is in an equal proportion in the reagent.

6. The reagent according to claim 5, wherein the reagent further comprises a reverse transcriptase.

7. A kit for a nucleic acid isothermal amplification via a polymerase spiral reaction for a target sequence amplification, comprising the set of primers according to claim 4.

8. A method for detecting a target nucleic acid molecule in a sample, the method, designated method A, comprising:
1) extracting nucleic acids from the sample;
2) performing an isothermal amplification at 60-65° C. for 120-150 mins using the reagent according to claim 5, and the nucleic acids as a template, to obtain amplification reaction products;
3) detecting the amplification reaction products using a real time turbidimeter instrument, if the real time turbidity detection curve of the amplification reaction products rises, the sample comprises or candidately comprises the target nucleic acid molecule;
wherein, if the real time turbidity detection curve of the amplification reaction products does not rise, the sample does not comprise or does not candidately comprise the target nucleic acid molecule.

9. The method according to claim 8, wherein the nucleic acid is either DNA or RNA.

10. A method for a nucleic acid isothermal amplification via a polymerase spiral reaction, the method comprising a pair of oligonucleotide primers, wherein nucleotide fragments that are the reverse of each other are added to each of a 5' end of the pair of oligonucleotide primers, wherein the nucleic acid isothermal amplification via the polymerase reaction is performed for a target gene using the pair of oligonucleotide primers and a DNA polymerase under isothermal conditions to self-spirally extend the target gene.

11. The method according to claim 10, wherein the pair of oligonucleotide primers for the polymerase spiral reaction comprises a pair of primers that comprises a forward primer FP and a backward primer BP,
the primer FP comprising an F region and an N region, the F region being complementary to an Fc region of the target gene, the N region being derived from the target gene, from an exogenous sequence, or a combination thereof, and is the same as the N region of 5' end of the BP primer;
the primer BP comprising a B region and an N region, the B region being complementary to a Bc region of the target gene, the N region being derived from the target gene, an exogenous sequence, or a combination thereof, and is the same as the N region of 5' end of the FP primer.

12. The method according to claim 11, wherein the method proceeds as follows:
   1) a self spiral ring structure is formed sequentially using the primers FP and BP; wherein:
      (1) the reaction is carried out in an isothermal environment of 60° C.–65° C., double strands of the target gene are unlocked into two single strands, the F region of the primer FP binds to the Fc portion of a single strand from 3' end to 5' end, and extends in the 3' direction to form a sequence Bc complementary to and forms a double stranded structure with the B region of the single strand from 3' end to 5' end, after which the double stranded structure is unlocked to form two single strands, wherein one of the strands is an intermediate single strand that comprises the N region, the F region and the Bc region from 5' end to 3' end, and the other strand is a single strand of the target gene from 3' end to 5' end;
      (2) the primer BP binds to the intermediate single strand that comprises the N region, the F region and the Bc region from 5' end to 3' end, B region in BP complementarily binds to the Bc region of the intermediate single strand, and extends in the 3' direction to form a double stranded structure comprising an Fc region complementary to the F region and an Nc region complementary to the N region, wherein when the double stranded structure is unlocked to form single strands, two single strands are formed, wherein one of the single strands is a target single strand of the target gene comprising the Nc region, the Fc region, the B region and the N region from 3' end to 5' end; and
      (3) the Nc region and the N region at two ends of the target single strand being complementary, form a self spiral ring structure when the Nc region binds to the N region, thus allowing a self spiral extension to be performed using the Nc region as a template, to generate spiral amplification products of various sizes, and to be completed in 5 minutes;
   2) and wherein, a self spiral ring structure may further be formed sequentially using primers BP and FP:
      (1) the reaction is carried out in an isothermal environment of 60° C.–65° C., double strands of the target gene are unlocked into two single strands, the B portion of the primer BP binds to the Bc portion of a single strand from 3' to 5' end, and extends in the 3' direction to form a sequence Fc complementary to and forms a double stranded structure with the F region of the single strand from 3' end to 5' end, after which the double stranded structure is unlocked to form two single strands, when one of the strands is an intermediate single strand that comprises the N region, the B region and the Fc region from 5' end to 3' end, and the other strand is a single strand of the target gene from 3' end to 5' end;
      (2) the primer FP binds the intermediate single strand that comprises the N region, the B region and the Fc region from 5' end to 3' end, F region in FP complementarily binds the Fc region of the intermediate single strand, and extends in 3' direction to form a double stranded structure comprising a Bc region complementary to the B region and an Nc region complementary to the N region, wherein when the double stranded structure is unlocked to form single strands, two single strands are formed, wherein one of the single strands is a target single strand of the target gene comprising the N region, the F region, the Bc region and the Nc region from 5' end to 3' end;
      (3) the Nc region and N region at two ends of the target single strand being complementary, form a self spiral ring structure when the Nc region binds to the N region, thus allowing a self spiral extension to be performed using the Nc region as a template, to generate spiral amplification products of various sizes, and to be completed in 5 minutes.

13. The method according to claim 12, wherein:
   the target gene is either NDM-1 gene or H1N1 gene;
   the FP primer for detecting NDM-1 gene is SEQ ID NO: 2, the BP primer is SEQ ID NO: 3;
   the FP primer for detecting H1N1 gene is SEQ ID NO: 5, the BP primer is SEQ ID NO: 6.

14. A method for detecting a target genome DNA in a sample by a nucleic acid isothermal amplification via a polymerase spiral reaction (PSR), comprising the following steps:
   1) preparing 23 µL of a PSR solution comprising: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8U Bst DNA polymerase, the amount of the PSR primers added is 40 pM for FP and BP, respectively;
   2) extracting nucleic acids from the sample to obtain a nucleic acid extraction solution whose concentration is greater than or equal to 20 ng/µL;
   3) adding 2 µL of the nucleic acid extraction solution to the PSR solution prepared in step 1) to make the final reaction volume be 25 µL, mixing the reaction solution, and adding a sealant to prevent contamination;
   4) performing the isothermal amplification reaction in an environment of 60-65° C., with a reaction time being 120-150 mins;
   5) recording by turbidimetry a change in turbidity in the reaction tube using a real time turbidimeter instrument, judging a sample whose curve rises as a positive result, and judging a sample whose curve does not rise as a negative result.

15. A method for detecting a target genome DNA in a sample by a nucleic acid isothermal amplification via a polymerase spiral reaction (PSR), comprising the following steps:
   1) preparing 23 µL of a PSR solution comprising: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8U Bst DNA polymerase, the amount of the PSR primers added is 40 pM for FP and BP, respectively;
   2) extracting nucleic acids from the sample to obtain a nucleic acid extraction solution whose concentration is greater than or equal to 20 ng/µL;
   3) adding 2 µL of the nucleic acid extraction solution and 1 µL of a color development solution to the PSR solution prepared in step 1) to make the final reaction volume be 26 µL, mixing the reaction solution, and adding a sealant to prevent contamination;
   4) performing an isothermal amplification reaction in a 60-65° C. environment, with a reaction time being 120-150 mins;
   5) observing a color development either with the naked eye or with the aid of ultraviolet light, judging a sample whose reaction solution has a color change as a positive result, and judging a sample whose reaction solution has no color change as a negative result.

16. A method for detecting an RNA in a sample by a nucleic acid isothermal amplification via a polymerase spiral reaction (PSR), comprising the following steps:
   1) preparing 23 μL of a PSR solution comprising: 20 mM Tris.HCl (pH 8.8), 10 mM KCl, 10 mM $(NH_4)_2SO_4$, 0.1% Tween 20, 0.8 M betaine, 8 mM $MgSO_4$, 1.4 mM dNTP each, 8U Bst DNA polymerase and reverse transcriptase, the amount of the PSR primers added is 40 pM for FP and BP, respectively;
   2) extracting nucleic acids from the sample to be detected to obtain a nucleic acid extraction solution whose concentration is greater than or equal to 20 ng/μL;
   3) adding 2 μL of the nucleic acid extraction solution to the PSR solution prepared in step 1), mixing the reaction solution, and adding a sealant to prevent contamination;
   4) performing an isothermal amplification reaction in a 60-65° C. environment, with reaction time being 120-150 mins;
   5) judging the reaction result using either a turbidimetry or a color development method.

17. A kit for a nucleic acid isothermal amplification via a polymerase spiral reaction for a target sequence amplification, comprising the reagent of claim 6.

18. A method of detecting a target nucleic acid molecule in a sample, the method comprising:
   providing the sample;
   providing the set of primers of claim 4;
   detecting the target molecule by a nucleic acid isothermal amplification via a polymerase spiral reaction.

19. The method of claim 18, further comprising the reagent of claim 6.

20. A kit of detecting a target nucleic acid molecule in a sample, the method comprising:
   providing the sample;
   providing the set of primers of claim 4;
   detecting the target molecule by a nucleic acid isothermal amplification via a polymerase spiral reaction.

21. The kit of claim 20, further comprising the reagent of claim 6.

22. A method for detecting a target nucleic acid molecule in a sample, the method, designated method B, comprising the steps of:
   1) extracting nucleic acids from the sample;
   2) performing an amplification using the reagent according to claim 5, and the nucleic acids as a template, and adding a chromogenic agent during amplification, to obtain amplification reaction products;
   3) observing the amplification reaction products by the naked eye, if the amplification reaction products develop a color, the sample comprises or candidately comprises the target nucleic acid molecule;
   if the amplification reaction products do not develop a color, the sample to be detected does not comprise or candidately does not comprise the target nucleic acid molecule.

23. The method according to claim 22, wherein the amplification condition is an isothermal reaction at 60-65° C. for 120-150 mins; and the nucleic acid is either DNA or RNA.

* * * * *

SEQUENCE LISTING

```
<160> NUMBER OF SEQ ID NOS: 8

<210> SEQ ID NO 1
<211> LENGTH: 813
<212> TYPE: DNA
<213> ORGANISM: Artificial
<220> FEATURE:
<223> OTHER INFORMATION: Synthetic

<400> SEQUENCE: 1
atggaattgc ccaatattat gcacccggtc gcgaagctga gcaccgcatt agccgctgca      60
ttgatgctga gcgggtgcat gcccggtgaa atccgcccga cgattggcca gcaaatggaa     120
actggcgacc aacggtttgg cgatctggtt ttccgccagc tcgcaccgaa tgtctggcag     180
cacacttcct atctcgacat gccgggtttc ggggcagtcg cttccaacgg tttgatcgtc     240
agggatggcg gccgcgtgct ggtggtcgat accgcctgga ccgatgacca gaccgcccag     300
atcctcaact ggatcaagca ggagatcaac ctgccggtcg cgctggcggt ggtgactcac     360
gcgcatcagg acaagatggg cggtatggac gcgctgcatg cggcggggat tgcgacttat     420
gccaatgcgt tgtcgaacca gcttgccccg caagagggga tggttgcagc gcaacacagc     480
ctgactttcg ccgccaatgg ctgggtcgaa ccagcaaccg cgcccaactt tggcccgctc     540
aaggtatttt accccggccc cggccacacc agtgacaata tcaccgttgg gatcgacggc     600
accgacatcg cttttggtgg ctgcctgatc aaggacagca aggccaagtc gctcggcaat     660
ctcggtgatg ccgacactga gcactacgcc gcgtcagcgc gcgcgtttgg tgcggcgttc     720
cccaaggcca gcatgatcgt gatgagccat tccgcccccg atagccgcgc cgcaatcact     780
catacggccc gcatggccga caagctgcgc tga                                  813

<210> SEQ ID NO 2
<211> LENGTH: 41
<212> TYPE: DNA
<213> ORGANISM: Artificial
<220> FEATURE:
<223> OTHER INFORMATION: Synthetic
```

<400> SEQUENCE: 2
acgattcgta catagaagta tagggtcgat accgcctgga c                         41

<210> SEQ ID NO 3
<211> LENGTH: 39
<212> TYPE: DNA
<213> ORGANISM: Artificial
<220> FEATURE:
<223> OTHER INFORMATION: Synthetic

<400> SEQUENCE: 3
gatatgaaga tacatgctta gcagcatgca gcgcgtcca                            39

<210> SEQ ID NO 4
<211> LENGTH: 182
<212> TYPE: DNA
<213> ORGANISM: Artificial
<220> FEATURE:
<223> OTHER INFORMATION: Synthetic

<400> SEQUENCE: 4
cagactaggc agatggtaca tgcaatgaga actattggga ctcatcctag ctccagtgct     60
ggtctgaaag atgaccttct tgaaaatttg caggcctacc agaagcgaat gggagtgcag    120
atgcagcgat tcaagtgatc ctctcgtcat tgcagcaaat atcattggga tcttgcacct    180
ga                                                                   182

<210> SEQ ID NO 5
<211> LENGTH: 45
<212> TYPE: DNA
<213> ORGANISM: Artificial
<220> FEATURE:
<223> OTHER INFORMATION: Synthetic

<400> SEQUENCE: 5
acgattcgta catagaagta taggcaatga gaactattgg gactc                     45

<210> SEQ ID NO 6
<211> LENGTH: 43
<212> TYPE: DNA
<213> ORGANISM: Artificial
<220> FEATURE:
<223> OTHER INFORMATION: Synthetic

<400> SEQUENCE: 6
gatatgaaga tacatgctta gcaatttgct gcaatgacga gag                       43

<210> SEQ ID NO 7
<211> LENGTH: 18
<212> TYPE: DNA
<213> ORGANISM: Artificial
<220> FEATURE:
<223> OTHER INFORMATION: Synthetic

<400> SEQUENCE: 7
tccagttgag gatctggg                                                   18

<210> SEQ ID NO 8
<211> LENGTH: 19
<212> TYPE: DNA
<213> ORGANISM: Artificial
<220> FEATURE:
<223> OTHER INFORMATION: Synthetic

```
<400> SEQUENCE: 8
gcatcaggac aagatgggc                                                      19
```